United States Patent
Fischer et al.

(12) 
(10) Patent No.: US 6,696,413 B2
(45) Date of Patent: *Feb. 24, 2004

(54) PHARMACEUTICAL PREPARATION WITH CYCLOSPORIN A

(75) Inventors: Wilfried Fischer, Holzkirchen (DE); Karin Klokkers, Holzkirchen (DE)

(73) Assignee: Hexal AG, Holzkirchen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 326 days.

This patent is subject to a terminal disclaimer.

(21) Appl. No.: 09/204,782

(22) Filed: Dec. 3, 1998

(65) Prior Publication Data

US 2001/0014665 A1 Aug. 16, 2001

Related U.S. Application Data

(63) Continuation-in-part of application No. 09/076,175, filed on May 11, 1998, now Pat. No. 6,022,852, which is a continuation-in-part of application No. 08/633,823, filed on Jun. 27, 1996, now abandoned.

(30) Foreign Application Priority Data

Jun. 16, 1995 (DE) .......................... 195 21 974

(51) Int. Cl.⁷ .............................. C07K 7/64; A61K 38/13
(52) U.S. Cl. ..................... 514/11; 514/458; 530/317; 549/410
(58) Field of Search .............. 514/11, 458; 530/317; 549/410

(56) References Cited

U.S. PATENT DOCUMENTS

| 4,388,307 | A | * | 6/1983 | Cavanak | 424/177 |
| 4,572,915 | A | * | 2/1986 | Crooks | 514/458 |
| 4,943,560 | A | * | 7/1990 | Wigness et al. | 514/11 |
| 4,970,076 | A | | 11/1990 | Horrobin | 424/456 |
| 5,583,105 | A | * | 12/1996 | Kovacs | 514/11 |
| 6,022,852 | A | * | 2/2000 | Klokkers et al. | 514/11 |

FOREIGN PATENT DOCUMENTS

| EP | 0 484 281 A2 | | 5/1992 |
| EP | 0 539 319 A2 | * | 4/1993 |
| GB | 2222770 A | * | 3/1990 |
| JP | 62-19512 | * | 1/1987 |
| WO | WO 87/02219 | | 4/1987 |
| WO | WO 95/01785 | * | 1/1995 |
| WO | WO95/11039 | * | 4/1995 |

OTHER PUBLICATIONS

G. Ismailos et al. 'Enhancemetn of Cyclosporin a Solubility by d–Alpha Tocopheryl–Polythylene Glycol 1000 Succinate (TPGS)' Pharmacuetical Research 1992, vol. 9 (Suppl.), p. s 224 (abs. PDD 7223), 1992.*

G. Ismailos et al., entitled Enhancement of Cyclosporin A Solubility by d–alphatocopheryl–polyethylene–glycol–1000 Succinate (TPGS), Pharmaceutical Research 1992, vol. 9 (Suppl.), p. S–224 (abs. PDD 7223).

D. Slakey et al., entitled Ascorbic Acid and α–Tocopherol Prolong Rat Cardiac Allograft Survival, Transplantation Proceedings 1993, vol. 25 (1, Book I), p. 610–611.

M.W. Adams, entitled D–Alpha Tocopherol Polyethelene Glycol 100 Succinate (Eastman Vitamin E TPGS) As An Emulsifier And Bio–Enhancer For Drugs And Lipophylic Compounds, Congr. Int. Technol. Pharm., 6th (1992), vol. 4, 254–62, published by: Assoc. Pharm. Galenique Ind., Chantenay Malabry, Fr.

M.de Lorgeril et al. entitled Effect of Dietary Supplementation with Alpha–Tocopherol on Platelet Aggregation and Cyclosporin Side–Effects in Heart Transplant Recipients, J. Mol. Cell.Cardiol. (25, Suppl. 4, S46, 1993).

* cited by examiner

Primary Examiner—Brenda Brumback
Assistant Examiner—Anish Gupta
(74) Attorney, Agent, or Firm—Cohen, Pontani, Lieberman & Pavane

(57) ABSTRACT

The invention relates to a pharmaceutical preparation which consists of or contains cyclosporin A, an emulsifying α-tocopherol derivative, an ethoxylation product of vegetable oils, fatty acids or fats as a further emulsifier and a pharmaceutically customary alcohol.

28 Claims, 1 Drawing Sheet

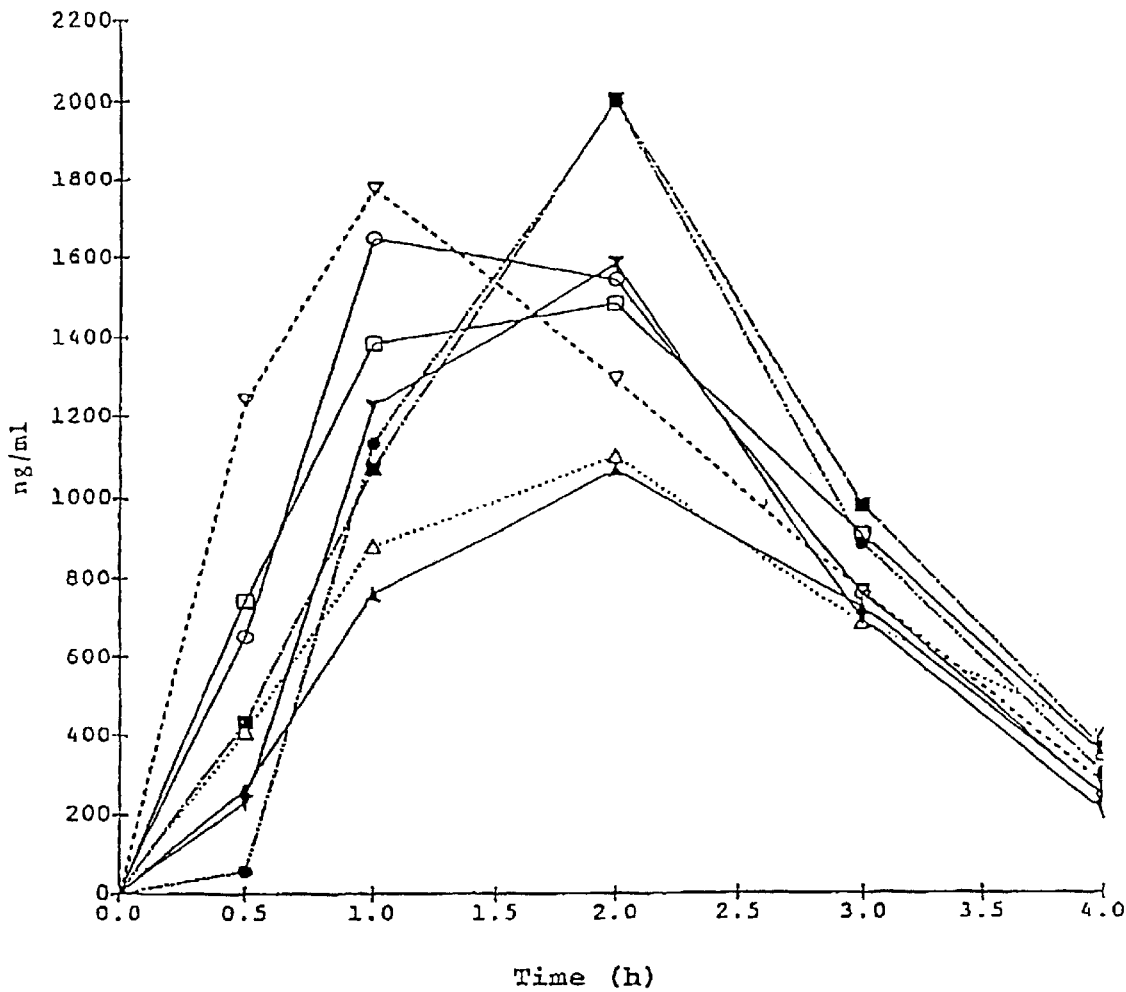

PHARMACEUTICAL PREPARATION WITH CYCLOSPORIN A

This application is a continuation-in-part of Ser. No. 09/076,175, filed May 11, 1998 now U.S. Pat. No. 6,022,852, which is a continuation-in-part of Ser. No. 08/633,823, filed Jun. 27, 1996, now abandoned.

FIELD OF THE INVENTION

The invention relates to pharmaceutical preparations which contain an effective amount of cyclosporin A in combination with emulsifying vitamin E derivatives and a further emulsifier.

PRIOR ART

Cyclosporin A is a cyclic, water-insoluble, non-polar undecapeptide. The compound is a highly effective immunosuppressant, obtained from fungal cultures (Cane et al., Transplant TROC. 13, 349–358 (1981); Ferguson et al., Surgery 92, 175–182 (1982)). The medicament is employed to prevent the rejection of transplanted allogenic organs (Bennett & Norman, Arzn. Rev. Med. 37, 215–224 (1986); Van Basen, Surg. Clin. North Am. 66, 435–449 (1986)). Its immunosuppressive effect is based on a selective inhibition of cell function, which allows a survival of, for example, heart transplants without myelocyte suppression (Myers et al., New England Journal of Medicine 311, 699 (1984)). Additionally to use in transplantations, more recent clinical trials have shown that cyclosporin A is effective in the treatment of a large number of autoimmune disorders. For example, clinical trials were carried out on the treatment of polymyositis, systemic lupus erythematosus, rheumatoid arthritis or even of juvenile insulin-dependent diabetes (see the corresponding chapter in: Cyclosporine in Autoimmune Diseases, Editor Schindler, Springer Verlag, Berlin 19985 [sic]).

Cyclosporin A is a lipophilic molecule having a molecular weight of 1,202 daltons. On account of the poor water solubility and the high lipophilicity of cyclosporin A, its pharmaceutical compositions with customary solid or liquid pharmaceutical excipients often have disadvantages. Thus the cyclosporins are not adequately absorbed from such compositions (Cavanak & Sucker, Formulation of Dosage Forms, Prog. Allergy 38, 65–72 (1986)), or the compositions are not well tolerated, or they are not adequately stable on storage, for example against the crystallization of cyclosporin. Often the dissolved concentration in relation to the dose of up to 1 g daily is low, e.g. only 3%, which means the administration of 30 g of solution. A higher solubility is mentioned in DE-B-2 907 460, in which a solution of cyclosporin in vegetable oil, such as olive oil or maize oil, ethanol and an emulsifier consisting of a non-ionic ester of a triglyceride with a polyalkylene glycol in described. Examples of the preferred compositions given by this patent are drinking solution, drinking emulsion, injection solution and solution in capsules.

The administration of the above composition is preferably carried out intramuscularly or subcutaneously or, in particular, orally. Cyclosporin A, administered with the above pharmaceutical forms, in distinguished by a good bioavailability. After absorption, the substance binds rapidly to plasma proteins and has a terminal half-life of 24 hours. It is metabolised to a high percentage in the liver, biliary excretion being the main elimination route (Beverige, Cyclosporin A; in: Proceedings of International Symposium, Cambridge, editor White, pages 35–44 (1982)).

In spite of the great value as an immunosuppressant, the clinical use of cyclosporin A is limited by the main side effect in chronic use, which is the nephrotoxicity of the active compound itself (Van Buren, Surg. Clin. North Am. 66, 435–449 (1986)). In about 80% of the kidney transplantation patients, renal toxicity also occurs (Kahan, Dial. Transplant. 12, 620–30 (1983)), mainly due to thin substance-inherent side effect, which is used for the protection of the transplant from rejection.

Frequent aide effects of cyclosporin treatments in various autoimmune disorders include, in addition to nephrotoxicity, hypertension, hyperkalaemia, hyperuricoaemia [sic], hepatotoxicity, anaemia, hypertrichiosis [sic], gingival hyperplasia, gastrointestinal side effects, tremor and paresthesia (Von Graffenried et al., Cyclosporine in Autoimmune Diseases, Editor Schindler, Springer Verlag, Berlin, pages 59–73 (1985)). Of the side effects mentioned here, the most frequent is nephrotoxicity. The acute nephrotoxicity induced by cyclosporin is dose-dependent and correlates with the cyclosporin blood levels. It is reversible after dose reduction or after completion of cyclosporin therapy (Chapman et al., Lancet I, 128 (1985)).

Acute cyclosporin nephrotoxicity is accompanied morphologically by tubular lesions wich are characterized by inclusion bodies, isometric vacuolization and microcalcification (Mihatsch et al., Transplant. Proc. 15, 2821 (1983)). This leads to a decrease in the glomerular filtration rate, as can be detected on the basis of the rapid rise of serum creatinine in cyclosporin-treated patients. A reason for this could be the perturbation of the dicrocirculation by interaction of cyclosporin with the local prostacyclin synthesis (Neild et al.; in: Cyclosporine, editor Kahan, Gruen & Stratton, Orlando, Fla., page 182 (1984)).

Although the mechanism of renal dysfunction has still not been completely clarified, it was possible to show that the renal synthesis of thromboxane occurs during the progress of immune- and non-immune-mediated models of renal damage (Lianos et al., J. Clin. Invest. 72, 1439–1448 (1983); Okegawa et al., J. Clin. Invest. 71, 81–90 (1983)). Thromboxane is a prostanoid and thus a metabolite of arachidonic acid from the cyclooxygenase cycle. The other prostanoids are prostaglandins and prostacyclins. Prostanoids are very effective mediators which are formed during immunologically generated inflammation processes. They can basically change the renal haemodynamics (Morley; in: Lymphokines, editor Pic, Academic Press, New York, 4, 377–391 (1981)).

EP-A-0 305 400 describes the connections between disordered prostanoid synthesis and nephrotoxicity. According to this the administration of cyclosporin is accompanied by an increased synthesis of thromboxane B2, a mediator of inflammations. Cyclosporin should accordingly also promote the formation of prostaglandins of the E series, also inflammation mediators. It was possible to connect the rejection of human kidney transplants with a rapid rise in renally eliminated thromboxane B2.

EP-A-0 305 400 furthermore describes the use of w3-unsaturated fatty acids [sic] in combination with cyclosporin A for the inhibition of prostaglandin or thromboxane formation.

A disadvantage of the longer-term w3-fatty acid [sic] administration in the formation of a vitamin E deficiency state. Deficiency states are, for example, haemolysis and a reduced lifetime of the erythrocytes. In animal experiments, vitamin E deficiency leads to degenerative muscle changes, creatinuria, increased haemolysis of the erythrocytes and to effects on certain hormones and enzymes and also protein and arachidonic acid metabolism (Machlin, Vitamin E; in: Machlin, Hand-book of Vitamins: Nutritional, Biochemical and Clinical Aspects, pages 99–145, Marcel Dekker, New York, 1984).

A further disadvantage of this combination with w3-unsaturated fatty acids [sic] (fish oils) is the obviously low active compound concentration to be achieved in this oil. Thus EP-A-0 305 400 describes only a concentration of 12.5 mg of cyclosporin A per gram of fish oil. In the case of a customary daily dose of more than 300 mg of cyclosporin A, this means a total administration amount of approximately 24 grams of the preparation and in the case of 1 g of cyclosporin A of 80 g of preparation. For patients, this is an unreasonably high amount of oil which would lead, for example encapsulated in soft gelatin capsules, to a daily administration of 24 capsules containing 300 mg of cyclosporin A. Parenteral administration by infusion would mean in an, optimistically calculated, 10 per cent oil-containing infusion emulsion an amount of about 240 ml of emulsion containing 300 mg of cyclosporin A, a volume which can only be infused over a relatively long time. Both aspects totally stand in the way of chronic administration, as is necessary in the case of transplantation patients.

The formulations according to DE-B-2 907 460 are indeed distinguished by a very high dissolving power for cyclosporin A, but have the disadvantage that they only include plant oils which contain no prostaglandin or thromboxane synthesis-inhibiting substances whatsoever. That means that the nephrotoxicity of cyclosporin A is not inhibited by the preparations. The commercially available parenteral solution of cyclosporin A (Sandimmun®) contains 50 mg of cyclosporin A, 32.9% of ethanol and 650 mg of Cremophor EL, an ethoxylated, hydrogenated castor oil, in 1 ml of solution. In addition to the amount of ethanol of 2 g per administration, which is a burden to the liver, according to literature reports Cremophor EL is nephrotoxic similar to cyclosporin A itself (Thiel et al., Clin. Nephrol. 25 (Suppl. 1), 540–542 (1986); Finn et al., Renal Failure 11, 3–15 (1989)). Thus Cremophor EL in the isolated, perfused rat kidney leads to a marked renal vasoconstriction with reduced renal blood flow and tubular dysfunction (Besarab et al., Transplantation 44, 195–201 (1987); Luke et al., Transplantation 43, 795–799 (1987)). In addition, Cremophor EL causes anaphylactic reactions up to shock (Chapuis et al., Engl. J. Med. 312, 1259 (1985), Leunissen et al., Lancet 1, 637 (1986); Magalini et al., Transplantation 42, 443–444 (1986)). The cause of the anaphylactoid reaction was regarded as Cremophor EL, as it leads to histamine liberation (Ennis et al., Agents Action 12, 64–80 (1982)). In some cases of therapy with the i.v. solution, the allergic reaction was observed on the first administration to humans (Friedmann et al., Am. J. Med. 70, 343–345 (1985); Magalini et al., Tansplantation 42, 443–444 (1986)). The disadvantage of the commerdially available parenteral preparation is accordingly the ingredient Cremophor EL. A formulation is therefore attempted which avoids the above side effects and increases the safety of the medicament.

The favourable immunosuppressive properties of cyclosporin A are utilized in the treatment of psoriasis. On account of its high molecular weight and its very high lipophilicity, however, cyclosporin A is not able to penetrate intact skin, especially the stratum corneum. For this reason, severe cases of psoriasis are treated by oral and parenteral cyclosporin administration. The disadvantage [sic] of this use are the systemic side effects on the circulation (hypertension) and the kidney function. Topical preparations for the treatment of psoriasis, with which the systemic side effects would be reduced, need absorption promoters, such as, for example, propylene glycol and azone (Duncan et al., British Journal of Dermatology 123, 631–640 (1990)). However, it is now especially known of azone that its permeation-promoting properties are to be attributed to a perturbation or even destruction of the protective function of the stratum corneum. Propylene glycol leads to a drying-out of the skin. Both substances would thus be more of a hindrance than a help in the healing of psoriasis. For this reason, a topical preparation having a therapeutically adequate cyclosporin A content in combination with substances promoting the healing process would be desirable. Moreover, the combination should promote the permeation of cyclosporin A through intact skin.

OBJECT OF THE INVENTION

The object of the present invention, then, is to find an advantageous solvent System which dissolves cyclosporin A in adequate amount, so that it can be taken orally in the therapeutically customary daily dose, can reduce the nephrotoxic effect and on topical application can promote both skin permeation and the healing process in the treatment of psoriasis.

BRIEF DESCRIPTION OF DRAWINGS

FIG. 1: The capsule preparation is equivalent to the commercially available product with respect to the blood levels.

DESCRIPTION OF THE INVENTION

The object on which the invention is based has now been achieved by a pharmaceutical preparation which consists of or contains cyclosporin A, an emulsifying α-tocopherol derivative, an ethoxylation product of vegetable oils, fatty acids or fats as a further emulsifier and a pharmaceutically customary alcohol.

This pharmaceutical preparation can be characterized by D-α-tocopherol polyethylene glycol 1000 succinate (vitamin E-TPGS) as α-tocopherol derivative.

The pharmaceutical preparation can furthermore be characterized by a content of α-tocopherol derivative of up to a 9-fold amount on the basis of cyclosporin A.

The pharmaceutical preparation can furthermore be characterized by a content of cyclosporin A of $\geqq 10\%$ on the basis of the composition.

The pharmaceutical preparation can furthermore be characterized by its content of ethanol or isopropanol as pharmaceutically customary alcohol, in particular in amounts of up to 30%.

The pharmaceutical preparation can furthermore be characterized by a content of ethoxylated castor oil as a further emulsifier.

The pharmaceutical preparation can furthermore be characterized by a content of thickener.

According to the invention, it was thus surprisingly found that emulsifying α-tocopherol derivatives, such as D-α- tocopherol polyethylene glycol 1000 succinate, have an excellent emulsifying or solvent power for cyclosporin A, and at the same time inhibit the synthesis of prostanoids such as prostaglandins and thromboxanes, which can be utilized to reduce nephrotoxicity and to cause inflammatory reactions in the skin to die down and at the same time promotes the absorption of cyclosporin A through the intact skin. The particular advantage of the solutions according to the invention consists, in addition to the achievement of high concentrations of dissolved cyclosporin A of at least 10%, in that the D-α-tocopherol derivatives, as derivative of natural vitamin E, have intrinsic effects which on the one hand counteract toxic effects of cyclosporin A at the customary high doses on oral administration and oil the other hand by means of the absorption-promoting action increase the intended immunosuppressive effect in the topical treatment of psoriasis.

Thus vitamin E and its derivatives affect arachidonic acid metabolism in the sense of an inhibition of prostaglandin, thromboxane and leucotriene biosynthesis and an increase in prostacyclin formation. These properties are connected with a biological inhibition of inflammation and with thrombotic disorders (Machlin, Vitamin E.; in: Machlin, Handbook of Vitamins: Ntritional [sic], Biochemical and Clinical Aspects, pages 99–145, Narcel Dekker, New York, 1984). After oral administration, vitamin E can also promote the activity of non-steroidal anti-inflammatory drugs (Bertolini et al., Rivista di Pharmakologia et Therapia 8, pages 27–34 (1982); Klein & Blankenhorn, Vergleich der klinischer Wirksamkeit von Vitamin E und Diclofenac Natrium bei Spondylitis Acylosans (Morbus Bechterew) [Comparison of the Clinical Activity of Vitamin E and Diclofenac Sodium in Ankylosing Spondylitis (Bechterew's disease)], Vitaminspur 2, pages 137–142 (1987)). After topical administration, vitamin E permeates the stratum corneum very well. Quantitative absorption studies were carried out on the skin of experimental animals. In this way, 16 hours after application of 300 μg of a 5 percent vitamin E solution in ethanol per $cm^2$, 10.7% of vitamin E was found in the horny layer and about 40.9% in underlying skin layers (Djerassi et al., Vitamin E: Biochemical function and its role in cosmetics, Drug & Cosmetic Industry 13, No. 1, pages 29–31, 34, 78 (198G)). Applied locally, vitamin E acts as a membrane-stabilizing antioxidant and inhibits the release of histamine and hydrolytic enzymes, for example from the mast cells and the lysosomes, by stabilization of their membranes. It also ingabits the synthesis of certain prostaglandins, deactivates oxygen radicals and detoxifies corresponding secondary products (Sien, Building von Superoxidradikalen und Peroxiden [Formation of superoxide Radicals and Peroxides]; in: Superoxiddismutase—Biochemie und therapeutischer Einsatz [Superoxide Disnmutase—Bio-chemistry and Therapeutic Use]; editors Puhl & Ries, Perimed Verlag, Erlangen, 1982). Vitamin E moreover increases the moistness of the skin and acts virtually as an occluding agent. All these described properties are advantageous in the treatment of psoriasis.

Cyclosporin A now dissolves completely unexpectedly in such a high concentration of ≧10% in preparations according to the invention that the combination can be therapeutically usefully emploved as a solution both in soft gelatin capsules and in topical formulations.

In addition, the formulations can contain thickeners, such as colloidal silicic acid or polyacrylic acid or polyacrylic acid derivatives or cellulose derivatives, as well as antioxidants and flavourings.

EXAMPLES

Example 1

Soft Gelatin Capsule

The composition of the formulation was as follows:

| | | |
|---|---|---|
| Cyclosporin A | 100 mg | |
| Ethyl alcohol 96% | 200 mg | |
| Vitamin E-TPGS | 300 mg | |
| Polyethoxylated castor oil | 200 mg | as ethoxylation product of a fat |
| Polyethylene glycol 400 | 200 mg | |

The mixture was filled into hard gelatin capsules [sic] and tested in a cross-over experiment in dogs in comparison with a commercially available product (Sandimmun optival®). The blood level analysis was carried out by means of fluorescence immuno-essay [sic].

It can be seen clearly from FIG. 1 that the capsule preparation according to the invention is equivalent to the commercially available product with respect to blood levels.

What is claimed is:

1. An oral pharmaceutical preparation in form of a solution comprising cyclosporin A; D-α-tocopherol polyethyleneglycol 1000 succinate as an emulsifying α-tocopherol derivative; a second emulsifier selected from the group consisting of the ethoxylates of fatty acids, vegetable oils, and fats; and a pharmaceutically acceptable alcohol.

2. The preparation of claim 1 wherein said α-tocopherol derivative is present in a ratio of cyclosporin A: α-tocopherol derivative of up to 1:9.

3. The pharmaceutical preparation of claim 1 wherein said cyclosporin A comprises about 10 weight percent of said preparation.

4. The pharmaceutical preparation of claim 2 wherein said cyclosporin A comprises about 10 weight percent of said preparation.

5. The preparation of claim 1 wherein said pharmaceutically acceptable alcohol comprises ethanol or isopropanol or mixtures thereof in amounts of up to 30% by weight of said preparation.

6. The preparation of claim 3 wherein said pharmaceutically acceptable alcohol comprises ethanol or isopropanol or mixtures thereof in amounts of up to 30% by weight of said preparation.

7. The preparation of claim 1 wherein said further emulsifier comprises ethoxylated castor oil.

8. The preparation of claim 2 wherein said further emulsifier comprises ethoxylated castor oil.

9. The preparation of claim 3 wherein said further emulsifier comprises ethoxylated castor oil.

10. The preparation of claim 5 wherein said further emulsifier comprises ethoxylated castor oil.

11. The preparation of claim 7 wherein said preparation further comprises an effective amount of a thickener.

12. An oral pharmaceutical preparation, comprising a solution of:
 (a) about 10 weight percent of cyclosporin A;
 (b) a first emulsifier comprising D-α-tocopherol polyethyleneglycol 1000 succinate;
 (c) a further emulsifier comprising ethoxylated castor oil; and
 (d) ethanol isopropanol or mixtures thereof in an amount up to about 30 weight percent of the solution.

13. The preparation of claim 12 further comprising an effective amount of a thickener.

14. An oral pharmaceutical preparation in form of a solution comprising cyclosporin A; D-α-tocopherol polyethyleneglycol 1000 succinate as an emulsifier; an ethoxylation product of fatty acids and fats; an alcohol selected from the group of ethanol and isopropanol; and optionally a thickener.

15. An oral pharmaceutical preparation in form of a solution consising essentially of cyclosporin A; D-α-tocopherol polyethyleneglycol 1000 succinate as an emulsifying α-tocopherol derivative; a second emulsifier selected from the group consisting of the ethoxylates of fatty acids, vegetable oils, and fats; and a pharamaceutical acceptable alcohol.

16. The preparation of claim 15 wherein said α-tocopherol derivative is present in a ratio of cyclosporin A: α-tocopherol derivative of up to 1:9.

17. The pharmaceutical preparation of claim 15 wherein said cyclosporin A comprises about 10 weight percent of said preparation.

18. The pharmaceutical preparation of claim 16 wherein said cyclosporin A comprises about 10 weight percent of said preparation.

19. The preparation of claim 15 wherein said pharmaceutically acceptable alcohol comprises ethanol or isopropanol or mixtures thereof in amounts of up to 30% by weight of said preparation.

20. The preparation of claim 17 wherein said pharmaceutically acceptable alcohol comprises ethanol or isopropanol or mixtures thereof in amounts of up to 30% by weight of said preparation.

21. The preparation of claim 15 wherein said further emulsifier comprises ethoxylated castor oil.

22. The preparation of claim 16 wherein said further emulsifier comprises ethoxylated castor oil.

23. The preparation of claim 17 wherein said further emulsifier comprises ethoxylated castor oil.

24. The preparation of claim 19 wherein said further emulsifier comprises ethoxylated castor oil.

25. The preparation of claim 21 wherein said preparation further comprises an effective amount of a thickener.

26. An oral pharmaceutical preparation, consisting essentially of a solution of:

a) about 10 weight percent of cyclosporin A;

b) a first emulsifier comprising D-α-tocopherol polyethylene glycol 1000 succinate c) a further emulsifier comprising ethoxylated castor oil; and d) ethanol, isopropanol, or mixtures thereof in an amount up to about 30 weight percent of the preparation.

27. The preparation of claim 26 further comprising an effective amount of a thickener.

28. An oral pharmaceutical preparation in form of a solution consisting essentially of cyclosporin A; D-α-tocopherol polycthyleneglycol 1000 succinate; an ethoxylation product of fatty acids and fats; an alcohol selected from the group consisting of ethanol and isopropanol; and optionally a thickener.

* * * * *